United States Patent
Okano et al.

(10) Patent No.: US 7,220,751 B2
(45) Date of Patent: May 22, 2007

(54) QUINAZOLINE DERIVATIVES AND DRUGS

(75) Inventors: Masahiko Okano, Nagaokakyou (JP); Kazuya Mori, Kyoto (JP)

(73) Assignee: Nippon Shinyaku Co., Ltd., Kyoto (JP)

( * ) Notice: Subject to any disclaimer, the term of this patent is extended or adjusted under 35 U.S.C. 154(b) by 281 days.

(21) Appl. No.: 10/399,803

(22) PCT Filed: Nov. 1, 2001

(86) PCT No.: PCT/JP01/09584

§ 371 (c)(1),
(2), (4) Date: Apr. 21, 2003

(87) PCT Pub. No.: WO02/36577

PCT Pub. Date: May 10, 2002

(65) Prior Publication Data

US 2004/0034044 A1    Feb. 19, 2004

(51) Int. Cl.
A61K 31/517 (2006.01)
C07D 413/02 (2006.01)
C07D 209/36 (2006.01)
C07C 29/20 (2006.01)
C07C 275/00 (2006.01)

(52) U.S. Cl. .............................. 514/266.4; 514/266.1; 514/266.2; 544/284

(58) Field of Classification Search ............ 514/266.2, 514/266.4, 234.5, 252.17, 266.1; 544/60, 544/116, 284, 293
See application file for complete search history.

(56) References Cited

U.S. PATENT DOCUMENTS

| | | | |
|---|---|---|---|
| 3,753,981 A | 8/1973 | Breuer et al. ................. 260/240 |
| 6,238,878 B1* | 5/2001 | Jakobsen et al. ............. 435/13 |
| 2004/0044204 A1* | 3/2004 | Mederski et al. ............. 544/60 |

FOREIGN PATENT DOCUMENTS

| DE | 2135172 | * | 1/1972 |
| DE | 2140280 | * | 2/1972 |
| EP | 0 579 496 A1 | | 1/1994 |
| WO | WO99/09986 | | 3/1999 |
| WO | WO01/72710 | | 10/2001 |
| WO | 02-24666 A2 | * | 3/2002 |

OTHER PUBLICATIONS

Zhikhareva et. al., Chemical Abstract, 1991, vol. 114, Abstract #95118d.*
Zhikhareva et. al., Chemical Abstract, 1985, vol. 102, Abstract #203929g.*
Zhikhareva et. al., Chemical Abstract, 1983, vol. 98, Abstract #16639x.*
Zhikhareva et. al., Chemical Abstract, 1982, vol. 96, Abstract #199625t.*
Zhikhareva et. al., Chemical Abstract, 1980, vol. 93, Abstract #114434v.*
Zhikhareva et. al., Chemical Abstract, 1980, vol. 93, Abstract #204585z.*
Fadeeva et. al., Chemical Abstract, 1987, vol. 107, Abstract #70301a.*
Botros et. al., Chemical Abstract, 1988, vol. 109, Abstract #211005n.*
Moshalenko et. al., Chemical Abstract, 1987, vol. 106, Abstract #32975v.*
Botros, S. et. al., "Synthesis of some 2-styrylquinazoline derivatives . . . ", Chem. Abs., 1979, vol. 90, Abstract # 54902.*

* cited by examiner

Primary Examiner—James O. Wilson
Assistant Examiner—Tamthom N. Truong
(74) Attorney, Agent, or Firm—Greenberg Traurig LLP; Gerard F. Diebner

(57) ABSTRACT

The invention provides an excellent novel analgesic which acts on a nociceptin receptor to exhibit a wide range of the analgesic effect for example on a chronic pain as well as an allodynia accompanied with a herpes zoster.

The invention relates to a nociceptin receptor agonist comprising as an active ingredient a compound represented by Formula (I) or a salt thereof:

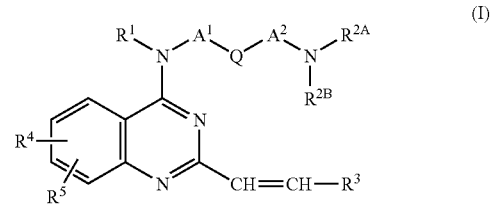

wherein $R^1$ represents a hydrogen atom or alkyl; $A^1$ and $A^2$ are the same or different and each represents a single bond or a divalent aliphatic hydrocarbon group; Q represents a single bond, cycloalkylene group, phenylene group or a divalent heterocyclic group; $R^{2A}$ and $R^{2B}$ are the same or different and each represents a hydrogen atom or alkyl; $R^3$ represents an optionally substituted phenyl group or heterocyclic group; $R^4$ and $R^5$ are the same or different and each represents a hydrogen atom, alkyl, alkoxy, aralkyloxy, halogen, nitro, hydroxy, alkoxycarbonyl, —$NR^6R^7$ and the like.

9 Claims, No Drawings

QUINAZOLINE DERIVATIVES AND DRUGS

TECHNICAL FIELD

The present invention relates to a pharmaceutically useful novel quinazoline derivative or a salt thereof, and a pharmaceutical composition containing the same as an active ingredient.

BACKGROUND ART

As an analgesic, a narcotic analgesic (such as morphine), a non-narcotic analgesic (such as aspirin or indomethacin) or a narco-antagonistic analgesic (such as pentazocine) is employed. A narcotic analgesic exerts its analgesic effect mainly by inhibiting a central algesic excitatory transmission. A non-narcotic analgesic exerts its analgesic effect mainly by inhibiting the production of a peripheral dolorogenic substance. A narco-antagonistic analgesic exerts its analgesic effect in a mechanism similar to that of a narcotic analgesic.

However, there is no analgesic which is effective against a chronic pain which is not suppressed by morphine, an allodynia accompanied with herpes zoster or a hyperalgesia, and an excellent analgesic has been desired to be created.

Nociceptin is a neuropeptide related to various nervous activities including an in vivo algesia. JP 10-212290 A describes that a nociceptin agonist and/or antagonist may be effective in treating a mental disorder, neuropathy and physiological disorder, and particularly effective in ameliorating anxiety and stress disorder, depression, traumatic disorder, amnesia due to Alzheimer's disease or other dementia, symptoms of epilepsy and spasm, acute and/or chronic pain, drug abuse withdrawal symptoms, water balance control, $Na^+$ excretion, arterial blood pressure disorder, and eating disorder such as an obesity.

As a non-peptide compound acting on a nociceptin receptor, lofentanil, naloxone benzoylhydrazone and 2-oxoimidazole derivative (WO98/54168) are known. However, these compounds are still at the stage of a basic research, and none of them has been commercially available.

Various quinazoline derivatives relating to a Compound (I) according to the present invention are known (WO93/07124, JP 2923742, WO98/50370, WO99/09986, JP 47-2927 A). Among such derivatives, 4-phenylmethylamino-2-[2-(3-pyridyl) vinyl]quinazoline disclosed in JP 2923742 is reported to have a cyclic GMP-phosphodiesterase inhibiting effect or thromboxan $A_2$ ($TXA_2$) synthetase inhibiting effect and to be useful in the prophylaxis and/or treatment of inflammations, hypertension, thrombosis, arterial sclerosis, cerebral hemorrhage, asthma, myocardial infarction, angina pectoris, cerebral infarction and the like. 4-(2-dimethylaminoethylamino)-6,7-dimethoxy-2-(E)-styrylquinazoline or 6,7-dimethoxy-4-[N-methyl-N-(3-dimethylamino) propylamino]-2-(E)-styrylquinazoline disclosed in WO99/09986 is reported to be useful as an insulin secretion promoter or diabetes treating agent. JP 47-2927 A describes that 4-(4-diethylamino-1-methyl) butylamino-2-(E)-(4-chlorostyryl) quinazoline is useful as an anti-inflammatory agent and the like.

DISCLOSURE OF THE INVENTION

An object of the present invention is to provide an excellent analgesic. Particularly, the present invention is intended to provide a novel analgesic having an analgesic effect which is effective widely against a chronic pain or an allodynia accompanied with herpes zoster by acting on a nociceptin receptor.

In order to achieve the above described objects, the present inventors found that compound represented by the following general formula (1) is an agonist and/or antagonist of a nociceptin receptor and has an excellent analgesic effect in processes to synthesize and study various compounds, thereby establishing the present invention.

Thus, the invention relates to a nociceptin receptor agonist or nociceptin receptor antagonist as well as an analgesic containing as an active ingredient a compound represented by Formula (I) or salt thereof:

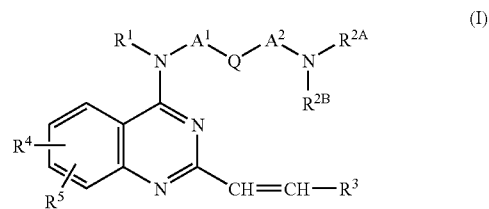

(I)

wherein, $R^1$ represents a hydrogen atom or alkyl;

$A^1$ and $A^2$ are the same or different and each represents (1) a single bond or (2) a divalent aliphatic hydrocarbon group which may be substituted and may contain 1 to 3 unsaturated bond at any positions (such an aliphatic hydrocarbon group may have a divalent group or heteroatom selected from the group consisting of —NH—, O and S);

Q represents (1) a single bond, (2) an optionally substituted 3- to 8-membered cycloalkylene group, (3) an optionally substituted phenylene group, or (4) an optionally substituted 4- to 8-membered divalent heterocyclic group;

$R^{2A}$ and $R^{2B}$ are the same or different and each represents a hydrogen atom or alkyl;

or represents a 5- to 7-membered ring as —N($R^1$)-$A^1$-Q-$A^2$-N($R^{2A}$)—;

$R^3$ represents an optionally substituted phenyl group or heterocyclic group;

$R^4$ and $R^5$ are the same or different and (1) each represents a hydrogen atom, alkyl, alkoxy, aralkyloxy, halogen, nitro, hydroxy, alkoxycarbonyl, —$NR^6R^7$, —$NR^6COR^7$, —$NR^6SO_2R^7$, —$CONR^6R^7$ (wherein $R^6$ and $R^7$ are the same or different and each represents a hydrogen atom or alkyl) or (2) adjacent $R^4$ and $R^5$ are taken together to form —O($CH_2$)$_n$O— (wherein n is an integer of 1 or 2) or —CH=CH—CH=CH—.

Preferably, in Formula (I), $R^1$ represents a hydrogen atom or alkyl;

$A^1$ and $A^2$ are the same or different and each represents (1) a single bond or (2) a divalent aliphatic hydrocarbon group which may be substituted by alkyl, carbamoyl, monoalkylcarbamoyl, dialkylcarbamoyl, hydroxy, alkoxy or trifluoromethyl (such an aliphatic hydrocarbon group may have a divalent group or heteroatom selected from the group consisting of —NH—, O and S and may contain 1 to 3 unsaturated bond at any positions);

Q represents (1) a single bond, (2) a 3- to 8-membered cycloalkylene group which may be substituted by alkyl, alkoxycarbonyl, carbamoyl, monoalkylcarbamoyl, dialkylcarbamoyl or alkoxy, (3) a phenylene group which may be substituted by alkyl, alkoxy, alkoxycarbonyl, carbamoyl, monoalkylcarbamoyl, dialkylcarbamoyl, sulfamoyl, monoalkylsufamoyl, dialkylsulfamoyl, amino, monoalkylamino, dialkylamino, nitro, halogen, cyano or trifluoromethyl, or (4) a 4- to 8-membered divalent heterocyclic group which may be substituted by alkyl, alkoxy, alkoxycarbonyl, carbamoyl, monoalkylcarbamoyl, dialkylcarbamoyl, amino, monoalkylamino or dialkylamino;

$R^{2A}$ and $R^{2B}$ are the same or different and each represents a hydrogen atom or alkyl;

or represents a 5- to 7-membered ring as —N($R^1$)-$A^1$-Q-$A^2$-N($R^{2A}$)—;

$R^3$ represents a phenyl group or heterocyclic group which may be substituted by alkyl, alkoxy, alkoxycarbonyl, carbamoyl, monoalkylcarbamoyl, dialkylcarbamoyl, sulfamoyl, monoalkylsufamoyl, dialkylsulfamoyl, alkylsulfonylamino, (N-alkyl)alkylsulfonylamino, amino, monoalkylamino, dialkylamino, nitro, halogen, cyano, hydroxy or trifluoromethyl;

$R^4$ and $R^5$ are the same or different and (1) each represents a hydrogen atom, alkyl, alkoxy, aralkyloxy, halogen, nitro, hydroxy, alkoxycarbonyl, —$NR^6R^7$, —$NR^6COR^7$, —$NR^6SO_2R^7$, —$CONR^6R^7$ (wherein each of $R^6$ and $R^7$ represents a hydrogen atom or alkyl) or (2) adjacent $R^4$ and $R^5$ are taken together to form —O(CH$_2$)$_n$O— (wherein n is an integer of 1 or 2) or —CH═CH—CH═CH—.

Furthermore, the invention relates to a compound represented by Formula (Ia) or a salt rhereof:

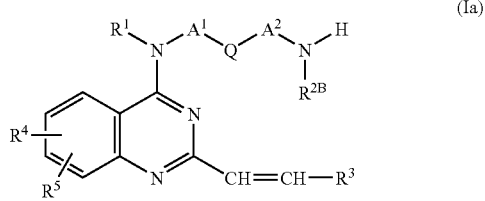

(Ia)

In the formula, $R^1$ represents a hydrogen atom or alkyl;

$A^1$ and $A^2$ are the same or different and each represents (1) a single bond or (2) a divalent aliphatic hydrocarbon group which may be substituted and may contain 1 to 3 unsaturated bond at any positions (such an aliphatic hydrocarbon group may have a divalent group or heteroatom selected from the group consisting of —NH—, O and S);

Q represents (1) a single bond, (2) an optionally substituted 3- to 8-membered cycloalkylene group, (3) an optionally substituted phenylene group, or (4) an optionally substituted 4- to 8-membered divalent heterocyclic group;

$R^{2B}$ represents a hydrogen atom or alkyl;

$R^3$ represents an optionally substituted phenyl group or heterocyclic group;

$R^4$ and $R^5$ are the same or different and (1) each represents a hydrogen atom, alkyl, alkoxy, aralkyloxy, halogen, nitro, hydroxy, alkoxycarbonyl, —$NR^6R^7$, —$NR^6COR^7$, —$NR^6SO_2R^7$, —$CONR^6R^7$ (wherein $R^6$ and $R^7$ are the same or different and each represents a hydrogen atom or alkyl) or (2) adjacent $R^4$ and $R^5$ are taken together to form —O(CH$_2$)$_n$O— (wherein n is an integer of 1 or 2) or —CH═CH—CH═CH—.

Preferably, in Formula (Ia), $R^1$ represents a hydrogen atom or alkyl;

$A^1$ and $A^2$ are the same or different and each represents (1) a single bond or (2) a divalent aliphatic hydrocarbon group which may be substituted by alkyl, carbamoyl, monoalkylcarbamoyl, dialkylcarbamoyl, hydroxy, alkoxy or trifluoromethyl (such an aliphatic hydrocarbon group may have a divalent group or heteroatom selected from the group consisting of —NH—, O and S and may contain 1 to 3 unsaturated bond at any positions);

Q represents (1) a single bond, (2) a 3- to 8-membered cycloalkylene group which may be substituted by alkyl, alkoxycarbonyl, carbamoyl, monoalkylcarbamoyl, dialkylcarbamoyl or alkoxy, (3) a phenylene group which may be substituted by alkyl, alkoxy, alkoxycarbonyl, carbamoyl, monoalkylcarbamoyl, dialkylcarbamoyl, sulfamoyl, monoalkylsufamoyl, dialkylsulfamoyl, amino, monoalkylamino, dialkylamino, nitro, halogen, cyano or trifluoromethyl, or (4) a 4- to 8-membered divalent heterocyclic group which may be substituted by alkyl, alkoxy, alkoxycarbonyl, carbamoyl, monoalkylcarbamoyl, dialkylcarbamoyl, amino, monoalkylamino or dialkylamino;

$R^{2B}$ represents a hydrogen atom;

$R^3$ represents a phenyl group or heterocyclic group which may be substituted by alkyl, alkoxy, alkoxycarbonyl, carbamoyl, monoalkylcarbamoyl, dialkylcarbamoyl, sulfamoyl, monoalkylsufamoyl, dialkylsulfamoyl, alkylsulfonylamino, (N-alkyl)alkylsulfonylamino, amino, monoalkylamino, dialkylamino, nitro, halogen, cyano, hydroxy or trifluoromethyl;

$R^4$ and $R^5$ are the same or different and (1) each represents a hydrogen atom, alkyl, alkoxy, aralkyloxy, halogen, nitro, hydroxy, alkoxycarbonyl, —$NR^6R^7$, —$NR^6COR^7$, —$NR^6SO_2R^7$, —$CONR^6R^7$ (wherein each of $R^6$ and $R^7$ represents a hydrogen atom or alkyl) or (2) adjacent $R^4$ and $R^5$ are taken together to form —O(CH$_2$)$_n$O— (wherein n is an integer of 1 or 2) or —CH═CH—CH═CH—.

A preferred Compound (I) or Compound (Ia) according to the invention may for example be cis-4-amino-cis-2-methyl-N-{6-methyl-2-[2-(2-pyridyl) ethenyl]quinazolin-4-yl}cyclohexylamine trihydrochloride (compound of Example 1), cis-4-[2-(4-chlorostyryl)-6-methylquinazolin-4-yl]aminocyclohexylamine dihydrochloride (Example 22), cis-2-[2-(4-chlorostyryl)-6-methoxyquinazolin-4-yl]aminocyclohexylamine dihydrochloride (Example 25), cis-4-{6-methyl-2-[2-(2-pyridyl) ethenyl]quinazolin-4-yl}aminocyclohexylamine trihydrochloride (Example 40), cis-4-{6-methoxy-2-[2-(2-pyridyl) ethenyl]quinazolin-4-yl}aminocyclohexylamine trihydrochloride (Example 44), cis-4-amino-cis-2-methyl-N-[2-(4-chlorostyryl)-6-methoxyquinazolin-4-yl]cyclohexylamine (Example 48), cis-4-amino-cis-2-methyl-N-{6-methoxy-2-[2-(3-pyridyl) ethenyl]quinazolin-4-yl}cyclohexylamine trihydrochloride (Example 50), cis-4-amino-cis-2-methyl-N-{6-methoxy-2-[2-(2-pyridyl) ethenyl]quinazolin-4-yl}cyclohexylamine trihydrochloride (Example 51), cis-4-amino-cis-2-methyl-N-{6-methyl-2-[2-(6-methyl-2-pyridyl) ethenyl]quinazolin-4-yl}cyclohexylamine trihydrochloride (Example 52), (1R, 2S, 4S)-4-amino-2-methyl-N-{6-methyl-2-[2-(2-pyridyl) ethenyl]quinazolin-4-yl}cyclohexylamine trihydrochloride (Example 57) and (1S, 2R, 4R)-4-amino-2-methyl-N-{6-methyl-2-[2-(2-pyridyl) ethenyl]quinazolin-4-yl}cyclohexylamine trihydrochloride (Example 58).

An feature of the invention is based on the discovery that a compound represented by Formula (I) (hereinafter referred to as a compound according to the invention) has a previously unknown nociceptin receptor agonistic or antagonistic effect.

The feature of a novel compound represented by Formula (Ia) (hereinafter referred to as an inventive compound) is characterized structurally by an unsubstituted amino group or a monoalkyl-substituted amino group present on the terminal of —N($R^1$)-$A^1$-Q-$A^2$— which is a substituent in the 4-position of the quinazoline backbone. A compound represented by Formula (Ia) is a novel compound which has not been reported in any publications. This compound is encompassed in Formula (I).

An inventive compound represented by Formula (I) or (Ia) acts on a nociceptin receptor and exhibits an excellent analgesic effect.

The invention is detailed below.

Examples of an "alkyl" in the present invention may include a straight or branched alkyl having 1 to 6 carbon atoms, for example, methyl, ethyl, n-propyl, isopropyl, n-butyl, isobutyl, sec-butyl, tert-butyl, n-pentyl, 5-isopentyl, n-hexyl, isohexyl and the like. Particularly, alkyl having 1 to 4 carbon atoms is preferable.

Examples of "alkoxy" may include a straight or branched alkoxy having 1 to 6 carbon atoms, for example, methoxy, ethoxy, n-propoxy, isopropoxy, n-butoxy, isobutoxy, sec-butoxy, tert-butoxy, n-pentyloxy, isopentyloxy, n-hexyloxy, isohexyloxy and the like. Particularly, alkoxy having 1 to 4 carbon atoms is preferable.

Examples of "aralkyloxy" may include aralkyloxy having 7 to 10 carbon atoms, for example, benzyloxy, phenetyloxy and the like. Particularly, benzyloxy is preferable.

Examples of a "divalent aliphatic hydrocarbon group" may include a straight or branched alkylene having 1 to 6 carbon atoms (for example, methylene, ethylene, trimethylene, tetramethylene, pentamethylene, hexamethylene, 2-ethyltrimethylene and 1-methyltetramethylene), a straight or branched alkenylene having 2 to 6 carbon atoms (for example, vinylene and propenylene) or a straight or branched alkynylene having 2 to 6 carbon atoms (for example, ethynylene). Such an aliphatic hydrocarbon group may contain one divalent group or heteroatom selected from a group consisting of NH, oxygen atom and sulfur atom.

Examples of a "cycloalkylene" may include cycloalkylene having 3 to 8 carbon atoms which may contain unsaturated bonds, for example, cyclopropylene, cyclobutylene, cyclopentylene, cyclohexylene, cycloheptylene and cyclooctylene, cyclohexenylene, cycloheptenylene, cyclooctenylene and the like. Such a cycloalkylene may have 1 to 2 substituents, and an example of such substituents may include alkyl, alkoxycarbonyl, carbamoyl, monoalkylcarbamoyl, dialkylcarbamoyl or alkoxy.

Examples of a "halogen" may include fluorine, chlorine, bromine and iodine atoms.

Examples of a heterocyclic ring in a "heterocyclic group" and "divalent heterocyclic group" may include a 4- to 8-membered monocyclic or fused ring which contains 1 to 2 heteroatoms selected from a group consisting of nitrogen atom, oxygen atom and sulfur atom, and which may have 1 to 4 unsaturated bonds. Examples of $R^3$ may include 2-pyridyl, 3-pyridyl, 4-pyridyl, 2-pyrimidinyl, 4-pyrimidinyl, 5-pyrimidinyl, 3-pyridazinyl, 4-pyridazinolyl, 2-pyrazinyl, 3-pyrazinyl and 3-indolyl. Such a heterocyclic group may have 1 to 2 substituents, and examples of the substituents may include alkyl, alkoxy, alkoxycarbonyl, carbamoyl, monoalkylcarbamoyl, dialkylcarbamoyl, sulfamoyl, monoalkylsulfamoyl, dialkylsulfamoyl, alkylsulfonylamino, N-(alkyl)alkylsulfonylamino, amino, monoalkylamino, dialkylamino, nitro, halogen, cyano, hydroxy or trifluoromethyl. Examples of a heterocyclic ring in a heterocyclic group Q may include pyridine, pyrimidine, piperazine, homopiperazine, furan, thiophene and the like. The heterocyclic group Q may have 1 to 2 substituents, and examples of such substituents may include alkyl, alkoxy, alkoxycarbonyl, carbamoyl, monoalkylcarbamoyl, dialkylcarbamoyl, amino, monoalkylamino or dialkylamino and the like.

A "phenylene group" may have 1 to 2 substituents, and examples of such substituents may include alkyl, alkoxy, alkoxycarbonyl, carbamoyl, monoalkylcarbamoyl, dialkylcarbamoyl, sulfamoyl, monoalkylsulfamoyl, dialkylsulfamoyl, amino, monoalkylamino, dialkylamino, hydroxy, nitro, halogen, cyano and trifluoromethyl.

An example of a ring represented by —N($R^1$)-$A^1$-Q-$A^2$—N($R^{2A}$)— may include a 5- to 7-membered saturated ring, such as piperazino or homopiperazino.

Examples of a "salt" may include a salt with an inorganic acid such as hydrochloric acid, sulfuric acid, nitric acid, phosphoric acid, hydrofluoric acid or hydrobromic acid and the like, or a salt with an organic acid such as acetic acid, tartaric acid, lactic acid, citric acid, fumaric acid, maleic acid, succinic acid, methanesulfonic acid, ethanesulfonic acid, benzenesulfonic acid, toluenesulfonic acid, naphthalenesulfonic acid or camphorsulfonic acid and the like.

A Compound (I) according to the invention may be present as a cis isomer (Z form) or a trans isomer (E form), and individual isomers and mixtures thereof are also encompassed in the invention.

Among Compounds (I) according to the invention, some may contain asymmetric carbon atoms, and individual optical isomers and racamic mixtures thereof are also encompassed in the invention. An optical isomer can be produced by an known optical resolution using an optically active acid (tartaric acid, dibenzoyltartaric acid, mandelic acid, 10-camphorsulfonic acid and the like) utilizing the basic nature of a starting racemic mixture obtained as described above or by starting from a previously prepared optically active compound.

An inventive compound represented by Formula (Ia) can be produced according to the following reaction steps:

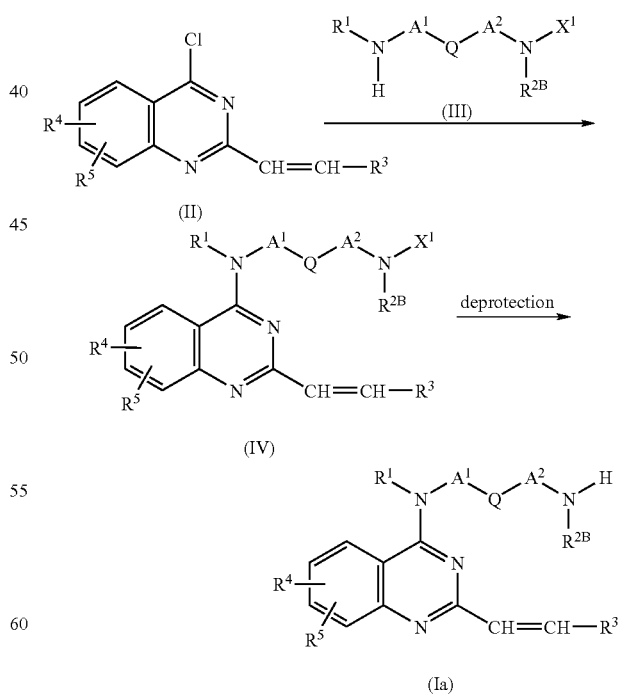

(wherein $R^1$, $A^1$, $A^2$, Q, $R^{2B}$, $R^3$, $R^4$ and $R^5$ are as defined above for the substituents in Formula (Ia) shown above. $X^1$ is protective group.)

A protecting group may for example be tert-butoxycarbonyl, methoxycarbonyl, ethoxycarbonyl, benzyloxycarbonyl and the like.

A Compound (II) is reacted with one equivalent to an excess of a Compound (III) in a solvent if necessary in the presence of a base (e.g., triethylamine, N,N-diisopropylethylamine) at a temperature from 0° C. to the boiling point of the solvent employed for a period of several hours to several days and then the deblocking is conducted by a method known per se to obtain a Compound (Ia). The solvent may for example be a hydrocarbon-based solvent such as benzene and toluene, an ether-based solvent such as dioxane and tetrahyfrofuran, a halogen-based solvent such as chloroform and 1,2-dichloroethane, an alcohol-based solvent such as ethanol and isopropanol, as well as N,N-dimethylformamide and the like. Preferably, 1 to 2 equivalent of a Compound (III) wherein $X^1$ is tert-butoxycarbonyl and $R^{2B}$ is a hydrogen atom is allowed to react in toluene as a solvent in the presence of triethylamine at 100° C. to 130° C. for 24 to 48 hours and then the deblocking is effected using trifluoroacetic acid or hydrochloric acid.

A Compound (Ia) thus produced can be isolated and purified by a method known per se such as concentration, liquid nature conversion, solvent extract, crystallization, recrystallization, fractional distillation, chromatography and the like.

A compound according to the invention represented by Formula (I) can be produced by the methods disclosed in WO93/07124, JP 2923742, WO98/50370, WO99/09986 and JP 47-2927 A.

A starting Compound (II) can be obtained in accordance with the description in pages 13 to 15 in WO99/09986.

A starting Compound (III) can be produced by a known method. For example, a Compound (IIIa) in which $R^1$ and $R^{2B}$ are hydrogen atoms, $A^1$ and $A^2$ are single bonds and Q is a 2-methylcyclohexylene group can be produced in accordance with the following reaction steps:

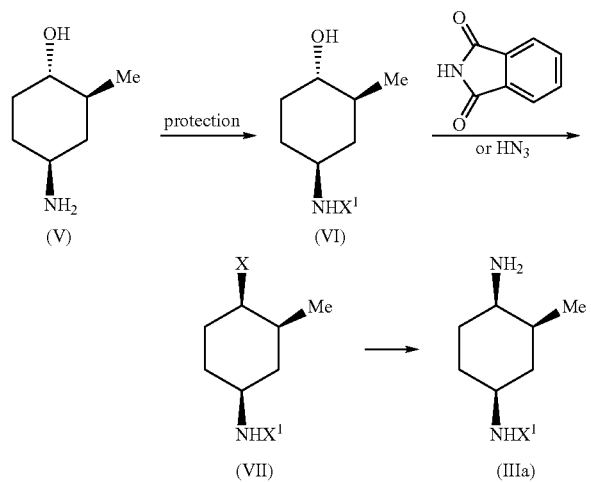

(wherein Me is methyl, $X^1$ is as defined above and X is a phthalimide group or azide group.)

(First Step)

A Compound (V) is protected by a method known per se to obtain a Compound (VI).

(Second Step)

The Compound (VI) is reacted with phthalimide or hydrogen azide in a solvent in the presence of triphenylphosphine and diethyl azodicarboxylate at a temperature of −40° C. to the boiling point of the solvent employed for a period of several hours to several days to obtain a Compound (VII). The solvent may for example be a hydrocarbon-based solvent such as benzene and toluene, an ether-based solvent such as dioxane and tetrahyfrofuran, a halogen-based solvent such as chloroform and 1,2-dichloroethane.

(Third Step)

The Compound (VII) is reduced or hydrolyzed by a method known per se which does not affect the protecting group $X^1$ to obtain a Compound (IIIa). In such a procedure, it is preferred that a Compound (VI) in which $X^1$ is tert-butoxycarbonyl is reacted with phthalimide in toluene as a solvent in the presence with triphenylphosphine and diethyl azodicarboxylate at 0° C. to 20° C. for 2 to 5 hours and then deprotected by a reaction with hydrazine in refluxing ethanol for 1 to 2 hours.

The Compound (V) can be produced by a known method (WO98/54157).

In the production method described above, an amino group or hydroxyl group can be protected if necessary by a protecting group employed customarily and then after the reaction described above the protecting group can be cleaved on an appropriate stage by a method known per se such as acid treatment, alkali treatment, catalytic hydrogenation and the like. The protecting group for an amino group may for example be benzyl, benzyloxycarbonyl, tert-butoxycarbonyl and trifluoroacetyl. The protecting group for a hydroxyl group may for example be methoxymethyl, 2-methoxyethoxymethyl, methylthiomethyl, tetrahydropyranyl, tert-butyl, benzyl, trimethylsilyl, tert-butyldimethylsilyl and the like.

A salt of a Compound (I) according to the invention can be produced by a method known per se. For example, a hydrochloride of a Compound (I) according to the invention can be obtained by treating the Compound (I) according to the invention with an alcohol solution or ethyl ether solution of hydrogen chloride followed by recovering the precipitated crystal by a filtration, or followed, if no precipitation occurs, by concentrating the solution to precipitate the crystal which is then recovered by a filtration.

Since a compound according to the invention represented by Formula (I) binds to a nociceptin receptor as described in the following Experiment Example to exert an agonistic or antagonistic effect, it is useful as an analgesic, anti-inflammatory agent, diuretic, anesthetic, antihypertensive, anxiolytic, anti-obese agent, auditory controlling agent, anti-depressive, anti-dementia agent and opioid analgesic tolerance-overcoming agent.

When a Compound (I) according to the invention is administered as a pharmaceutical, the Compound (I) according to the invention is administered as it is or in the form of a pharmaceutical composition containing it for example at 0.1% to 99.5%, preferably 0.5% to 90% in a pharmaceutically acceptable non-toxic and inert carrier to mammalian animals including human.

As a carrier, one or more of solid, semi-solid or liquid diluents, fillers and other formulation auxiliary agents are employed. A pharmaceutical composition is administered preferably in a unit dosage form. Among Compounds (I) according to the invention, a water-soluble compound can be employed not only as a solid formulation but also as a liquid formulation (e.g., intravenous injection formulation, intrabladder infusion formulation, oral syrup). A pharmaceutical composition can be given by an intra-tissue administration, oral administration, topical administration (Such as percutaneous administration) or rectal administration. It is a matter of course that dosage forms suitable to relevant administration modes are employed. For example, an oral or intravenous administration is preferred.

The dose as an analgesic is adjusted as appropriate on the basis of the age, body weight, conditions such as disease nature and severity of the patient as well as the administration mode, and it is usually 1 mg to 1000 mg, preferably 1 mg to 500 mg, daily as an active ingredient of a Compound (I) according to the invention when given intravenously to an adult. In some cases, a lower dose may be sufficient or a higher dose may be required. Usually, the dose may be given once a day or divided into several portions, or continuously over a period of 1 to 24 hours a day via an intravenous administration.

The oral administration can be accomplished by using a solid or liquid dosage unit, for example in the dosage form of a pellet, powder, tablet, sugar-coated tablet, capsule, granule, suspension, liquid, syrup, drop, buccal formulation, suppository and other dosage forms. The pellet is produced by pulverizing an active substance into a suitable particle size. The powder is produced by pulverizing an active substance into a suitable particle size and then mixing with a similarly pulverized pharmaceutical carrier, for example, an edible carbohydrate such as a starch and mannitol, together with other optional materials. If necessary, a seasoning, preservative, dispersant, colorant, flavor and other additives may be mixed.

A capsule is produced by filling a pellet or powder which had been pulverized as described above or a granule obtained as described below in the section of a tablet for example in an encapsulating shell such as a gelatin capsule. The filling may be accomplished after mixing the pulverized material with a lubricant, fluidizing agent, such as colloidal silica, talc, magnesium stearate, calcium stearate, solid polyethylene glycol and the like. The availability of a pharmaceutical after being ingested can be improved by adding a disintegrant or solubilizing agent, such as carboxymethyl cellulose, calcium carboxymethyl cellulose, low-substituted hydroxypropyl cellulose, sodium croscarmellose, sodium carboxy starch, calcium carbonate, sodium carbonate and the like.

A microparticle of an inventive compound may be suspended and dispersed in a vegetable oil, polyethylene glycol, glycerin or surfactant, and then enclosed in a gelatin sheet to produce a soft capsule. A tablet is produced by preparing a powder mixture, converting into a granule or slug, adding a disintegrant or lubricant and then compacting into a tablet. For the powder mixture, a suitably pulverized substance is mixed with a diluent or formulation base described above together if necessary with a binder (for example, sodium carboxymethyl cellulose, hydroxypropyl cellulose, methyl cellulose, hydroxypropylmethyl cellulose, gelatin, polyvinyl pyrrolidone, polyvinyl alcohol and the like), a dissolution retardant (for example, paraffin, wax, hardened castor oil and the like), a reabsorption agent (for example, quaternary salt) or a adsorbent (for example, bentonite, kaolin, dicalcium phosphate and the like). The powder mixture can be granulated by wetting it with a binder such as syrup, starch glue, gum arabic, cellulose solution or polymeric material solution and then passing it forcibly through a sieve. Instead of granulating the powder as described above, the powder may be subjected first to a tabletting machine to obtain an incompletely shaped slug which is then pulverized to obtain a granule.

A granule thus obtained can be prevented from being adhered with each other by adding a lubricant such as stearic acid, stearate, talc, mineral oil and the like. The mixture thus lubricated is then compacted into a tablet.

A plane tablet thus obtained may then be film-coated or sugar-coated.

A pharmaceutical may also be compacted directly into a tablet after mixing with a fluidized inert carrier instead of being subjected to the process for forming a granule or slug as described above. A transparent or semi-transparent protective film as a closely shielding shellac coating, a sugar or polymeric film or a wax polisher film may also be employed.

Any of other oral formulations such as a solution, syrup and elixir may be produced as a unit dosage form containing a certain amount of a pharmaceutical in a certain amount of the formulation. A syrup is produced by dissolving a compound in a suitable flavored aqueous solution, and an elixir is produced by using a non-toxic alcoholic carrier. A suspension is formulated by dispersing a compound in a non-toxic carrier. If necessary, a solubilizing agent or emulsifier (for example, ethoxylated isostearyl alcohols, polyoxyethylene sorbitol esters), preservative, seasoning (for example, peppermint oil, saccharin) and other additives may be added.

A unit dosage form for an oral administration may be formulated as a microcapsule if necessary. Such a form may be imparted with a prolonged duration of the activity and a sustained release profile by coating it with a film or embedding it in a polymer or wax.

An intra-tissue administration can be accomplished by using a liquid unit dosage form as a subcutaneous, intramuscular, intrabladder or intravenous injection formulation, such as a solution or suspension formulation. Any of these formulations is produced by suspending or dissolving a certain amount of a compound in a non-toxic liquid carrier suitable for the purpose of the injection such as an aqueous or oily solvent followed by sterilizing the suspension or solution. Alternatively, a certain amount of a compound is taken into a vial which is then sterilized together with its content and then sealed. For dissolving or mixing just before administration, a powder or lyophilized active component may be provided in combination with auxiliary vial and carrier. A non-toxic salt or salt solution may be added to obtain an isotonic formulation for injection. It is also possible to add stabilizers, preservatives and emulsifiers.

A rectal administration can be accomplished by using a suppository prepared by mixing a compound with a water-soluble or insoluble solid, such as polyethylene glycol, cocoa butter, higher esters (for example, myristyl palmitate) and a mixture thereof.

BEST MODE FOR CARRYING OUT THE INVENTION

The invention is further detailed with referring to the Production Examples (Reference Examples) of representative starting compounds, the Production Examples (Examples) of inventive compounds, the Formulation Examples and the Experiment Examples, which are not intended to restrict the invention. An specific optical rotation was measured at 20° C. The structure of the Compound of an Example was identified by MS, NMR and elemental analysis.

REFERENCE EXAMPLE 1 cis-4-tert-butoxycarbonylamino-cis-2-methylcyclohexylamine

Step 1 trans-4-tert-butoxycarbonylamino-trans-2-methylcyclohexanol

To a solution of 1.0 g of trans-4-amino-trans-2-methylcyclohexanol in 20 ml of chloroform, a solution of 2.53 g of di-tert-butyl dicarbonate in 10 ml of chloroform was added dropwise and the mixture was stirred for 15 hours at room temperature. The reaction mixture was concentrated, and the residue was purified by a silica gel chromatography (n-hexane:ethyl acetate=2:1) to obtain a crystal which was washed with diisopropyl ether to obtain 0.97 g of the intended compound.

Step 2 cis-4-tert-butoxycarbonylamino-cis-2-methyl-N-phthaloylcyclohexylamine

To 50 ml of a toluene solution of 0.97 g of trans-4-tert-butoxycarbonylamino-trans-2-methylcyclohexanol, 1.35 g of triphenylphosphine was added and the mixture was treated dropwise with 0.75 g of phthalimide and 2.22 g of a 40% solution of diethyl azodicarboxylate in toluene with cooling on ice and then stirred at room temperature overnight. The reaction solution was concentrated, and the residue was purified on a silica gel column (n-hexane:ethyl acetate=4:1) to obtain 1.25 g of the intended compound.

Step 3 cis-4-tert-butoxycarbonylamino-cis-2-methylcyclohexylamine

To 40 ml of an ethanol suspension of 1.25 g of cis-4-tert-butoxycarbonylamino-cis-2-methyl-N-phthaloylcyclohexylamine, 1.00 g of hydrazine monohydrate was added and the mixture was stirred at 80° C. for 2 hours. After distilling the solvent off, the residue was combined with 10% sodium hydroxide, extracted with chloroform, dried over sodium sulfate and then concentrated. The residue was purified by a silica gel column chromatography (chloroform:methanol=10:1) to obtain 0.75 g of the intended compound.

REFERENCE EXAMPLE 2

(1R, 2S, 4S)-4-tert-butoxycarbonylamino-2-methyl-cyclohexylamine

Step 1 trans-4-benzoyloxy-N-tert-butoxycarbonyl-cis-3-methylcyclohexylamine

A solution of 0.54 g of trans-4-tert-butoxycarbonylamino-trans-2-methylcyclohexanol in 15 ml of methylene chloride was treated dropwise with 0.358 g of triethylamine, 0.356 ml of benzoyl chloride with cooling on ice and then stirred at room temperature for 15 hours. The reaction solution was combined with water, extracted with methylene chloride, dried over magnesium sulfate and concentrated. The residue was purified by a silica gel column chromatography (n-hexane:ethyl acetate=5:1) to obtain 0.61 g of the intended compound.

Step 2

(1S, 2S, 4S)-4-tert-butoxycarbonylamino-2-methyl-cyclohexanol trans-4-benzoyloxy-N-tert-butoxycarbonyl-cis-3-methylcyclohexylamine was resolved optically using an optically active column (DAICEL CHIRALPAK AD column; n-hexane:isopropyl alcohol:diethylamine=970:30:1) and a compound was obtained from a preceding fraction which had $[\alpha]_D^{20}$+37.78 (c=1.0, methanol). From the resultant compound, the benzoyl group was cleaved in methanol using a 10% aqueous solution of sodium hydroxide to obtain the intended compound. The absolute configuration was identified by NMR after converting the resultant alcohol into the corresponding ester by means of a reaction with (+)-α-methoxy-α-(trifluoromethyl) phenylacetyl chloride and (−)-α-methoxy-α-(trifluoromethyl) phenylacetyl chloride.

Step 3

(1R, 2S, 4S)-4-tert-butoxycarbonylamino-2-methyl-N-phthaloylcyclohexylamine

Similarly to Step 2 in Reference Example 1 and starting from (1S, 2S, 4S)-4-tert-butoxycarbonylamino-2-methylcyclohexanol, the intended compound was obtained.

Step 4

(1R, 2S, 4S)-4-tert-butoxycarbonylamino-2-methyl-cyclohexylamine

Similarly to Step 3 in Reference Example 1 and starting from (1R, 2S, 4S)-4-tert-butoxycarbonylamino-2-methyl-N-phthaloylcyclohexylamine, the intended compound was obtained.

REFERENCE EXAMPLE 3

(1S, 2R, 4R)-4-tert-butoxycarbonylamino-2-methyl-cyclohexylamine

Similarly to Steps 2, 3 and 4 in Reference Example 2 and starting from the subsequent fraction of $[\alpha]_D^{20}$−39.94 (c=1.0, methanol) obtained in Step 2 in Reference Example 2, the intended compound was obtained.

EXAMPLE 1 cis-4-amino-cis-2-methyl-N-{6-methyl-2-[2-(2-pyridyl) ethenyl]quinazolin-4-yl}cyclohexylamine Trihydrochloride Step 1 cis-4-tert-butoxycarbonylamino-cis-2-methyl-N-{6-methyl-2-[2-(2-pyridyl) ethenyl]quinazolin-4-yl}cyclohexylamine 10 ml of a toluene solution of 70 mg of 4-chloro-6-methyl-2-[2-(2-pyridyl) ethenyl]quinazoline, 60 mg of cis-4-tert-butoxycarbonylamino-cis-2-methylcyclohexylamine and 100 mg of triethylamine was combined with a catalytic amount of 4-dimethylaminopyridine and heated under reflux for 24 hours. After distilling the reaction solution off, the residue was combined with water, extracted with chloroform, dried over magnesium sulfate and concentrated. The residue was purified by a silica gel column chromatography (chloroform:methanol=50:1) to obtain 50 mg of intended compound.

Step 2 cis-4-amino-cis-2-methyl-N-{6-methyl-2-[2-(2-pyridyl) ethenyl]quinazolin-4-yl}cyclohexylamine Trihydrochloride A solution of 50 mg of cis-4-tert-butoxycarbonylamino-cis-2-methyl-N-{6-methyl-2-[2-(2-pyridyl) ethenyl]quinazolin-4-yl}cyclohexylamine in 3 ml of methanol and 3 ml of chloroform was combined with 5 ml of a 4N solution of hydrogen chloride in ethyl acetate and reacted at 50° C. for 48 hours. After concentration followed by crystallization from ethyl acetate, 40 mg of the intended compound was obtained as a pale yellow powder.

Positive ion FAB-MS m/z: 374[M+H]$^+$

Similarly to Example 1, the following compounds were produced.

EXAMPLE 2

N-[2-(4-chlorostyryl)quinazolin-4-yl]-1,2-ethylenediamine dihydrochloride

Positive ion FAB-MS m/z: 325[M+H]$^+$ Appearance: White powder

EXAMPLE 3

N-[2-(4-chlorostyryl)quinazolin-4-yl]-1,4-butanediamine dihydrochloride

Positive ion FAB-MS m/z: 353[M+H]$^+$ Appearance: White crystal

EXAMPLE 4

N-[2-(4-chlorostyryl)quinazolin-4-yl]-1,5-pentanediamine dihydrochloride

Positive ion FAB-MS m/z: 367[M+H]$^+$ Appearance: White powder

EXAMPLE 5

N-[2-(4-chlorostyryl)quinazolin-4-yl]-1,6-hexanediamine dihydrochloride

Positive ion FAB-MS m/z: 381[M+H]$^+$ Appearance: White powder

EXAMPLE 6

N-[6-chloro-2-(4-chlorostyryl)quinazolin-4-yl]-1,6-hexanediamine dihydrochloride Positive ion FAB-MS m/z: 415[M+H]$^+$

EXAMPLE 7

N-[2-(4-chlorostyryl)-6-methylquinazolin-4-yl]-1,6-hexanediamine dihydrochloride Positive ion FAB-MS m/z: 395[M+H]$^+$

EXAMPLE 8

N-[2-(4-chlorostyryl)-6-methylquinazolin-4-yl]-1,4-butanediamine dihydrochloride Positive ion FAB-MS m/z: 367[M+H]$^+$ White powder

EXAMPLE 9

N-[2-(4-chlorostyryl)-6,7-difluoroquinazolin-4-yl]-1,6-hexanediamine dihydrochloride Positive ion FAB-MS m/z: 417[M+H]$^+$ White powder

EXAMPLE 10

N-[2-(4-chlorostyryl)quinazolin-4-yl]-1,8-octanediamine dihydrochloride

Positive ion FAB-MS m/z: 409[M+H]$^+$ Appearance: Pale red powder

EXAMPLE 11 trans-2-[2-(4-chlorostyryl)-6-methylquinazolin-4-yl] aminocyclohexylamine dihydrochloride Positive ion FAB-MS m/z: 393[M+H]$^+$ Appearance: Pale yellow powder

EXAMPLE 12 cis-2-[2-(4-chlorostyryl)-6-methylquinazolin-4-yl] aminocyclohexylamine dihydrochloride Positive ion FAB-MS m/z: 393[M+H]$^+$ Appearance: Dark pale yellow powder

EXAMPLE 13

N-[2-(4-chlorostyryl)-5-methylquinazolin-4-yl]-1,6-hexanediamine dihydrochloride Positive ion FAB-MS m/z: 395[M+H]$^+$

EXAMPLE 14

N-[2-(4-chlorostyryl)-8-methylquinazolin-4-yl]-1,6-hexanediamine dihydrochloride Positive ion FAB-MS m/z: 395[M+H]$^+$

EXAMPLE 15

N-[2-(4-chlorostyryl)quinazolin-4-yl]-1,4-diamino-2-butene dihydrochloride

Positive ion FAB-MS m/z: 351[M+H]$^+$ Appearance: Pale yellow crystal

EXAMPLE 16

N-[2-(4-chlorostyryl)-6-methylquinazolin-4-yl]-1,2-ethylenediamine dihydrochloride Positive ion FAB-MS m/z: 339[M+H]$^+$ White powder

EXAMPLE 17

N-[2-(4-chlorostyryl)-7-methylquinazolin-4-yl]-1,6-hexanediamine dihydrochloride Positive ion FAB-MS m/z: 395[M+H]$^+$

EXAMPLE 18

N-[2-(4-chlorostyryl)-6-tert-butylquinazolin-4-yl]-1,6-hexanediamine dihydrochloride Positive ion FAB-MS m/z: 437[M+H]$^+$ Appearance: White powder

EXAMPLE 19

N-[2-(4-chlorostyryl)-6-hydroxyquinazolin-4-yl]-1,6-hexanediamine dihydrochloride Positive ion FAB-MS m/z: 397[M+H]$^+$ Orange yellow powder

EXAMPLE 20

N-[2-(3-indolylethenyl)-6-methylquinazolin-4-yl]-hexane-1,6-hexanediamine dihydrochloride Positive ion FAB-MS m/z: 400[M+H]$^+$

EXAMPLE 21

N-[2-(4-chlorostyryl)-6-methoxyquinazolin-4-yl]-1,6-hexanediamine dihydrochloride Positive ion FAB-MS m/z: 411[M+H]$^+$

EXAMPLE 22 cis-4-[2-(4-chlorostyryl)-6-methylquinazolin-4-yl] aminocyclohexylamine dihydrochloride Positive ion FAB-MS m/z: 393[M+H]$^+$

EXAMPLE 23

N-[2-(4-chlorostyryl)-6,7-dimethylquinazolin-4-yl]-1,5-pentanediamine dihydrochloride Positive ion FAB-MS m/z: 395[M+H]$^+$

EXAMPLE 24

N-[2-(4-chlorostyryl)-6-isopropylquinazolin-4-yl]-1,6-hexanediamine dihydrochloride Positive ion FAB-MS m/z: 423[M+H]$^+$

EXAMPLE 25 cis-2-[2-(4-chlorostyryl)-6-methylquinazolin-4-yl] aminocyclohexylamine dihydrochloride Positive ion FAB-MS m/z: 409[M+H]$^+$

EXAMPLE 26 cis-2-[2-(4-chlorostyryl)-6-isopropylquinazolin-4-yl] aminocyclohexylamine dihydrochloride Positive ion FAB-MS m/z: 421[M+H]$^+$

EXAMPLE 27 cis-4-[2-(4-chlorostyryl)-6-isopropylquinazolin-4-yl] aminocyclohexylamine dihydrochloride Positive ion FAB-MS m/z: 421[M+H]$^+$

EXAMPLE 28 cis-4-[2-(4-chlorostyryl)-6-methoxyquinazolin-4-yl] aminocyclohexylamine dihydrochloride Positive ion FAB-MS m/z: 409[M+H]$^+$

EXAMPLE 29 cis-4-[2-(4-chlorostyryl)-6-ethylquinazolin-4-yl] aminocyclohexylamine dihydrochloride Positive ion FAB-MS m/z: 407[M+H]$^+$

EXAMPLE 30 cis-3-[2-(4-chlorostyryl)-6-methylquinazolin-4-yl] aminocyclohexylamine dihydrochloride Positive ion FAB-MS m/z: 393[M+H]$^+$

EXAMPLE 31 trans-3-[2-(4-chlorostyryl)-6-methylquinazolin-4-yl] aminocyclohexylamine dihydrochloride Positive ion FAB-MS m/z: 393[M+H]$^+$

EXAMPLE 32 cis-2-[2-(4-chlorostyryl)-6-hydroxyquinazolin-4-yl] aminocyclohexylamine dihydrochloride Positive ion FAB-MS m/z: 395[M+H]$^+$ Yellow powder

EXAMPLE 33 cis-2-[6-benzyloxy-2-(4-chlorostyryl)quinazolin-4-yl]aminocyclohexylamine dihydrochloride Positive ion FAB-MS m/z: 485[M+H]$^+$ Pale green powder

EXAMPLE 34 cis-4-{6-methyl-2-[2-(4-pyridyl) ethenyl]quinazolin-4-yl}aminocyclohexylamine Trihydrochloride Positive ion FAB-MS m/z: 360[M+H]$^+$

EXAMPLE 35 cis-4-[2-(4-chlorostyryl)-6-methoxyquinazolin-4-yl]
aminomethylcyclohexylamine dihydrochloride Positive ion FAB-MS m/z: 423[M+H]$^+$

EXAMPLE 36 trans-4-[2-(4-chlorostyryl)-6-methylquinazolin-4-yl]
aminocyclohexylamine dihydrochloride Positive ion FAB-MS m/z: 393[M+H]$^+$

EXAMPLE 37 cis-4-{6-methyl-2-[2-(3-pyridyl) ethenyl]quinazolin-
4-yl}aminocyclohexylamine Trihydrochloride Positive ion FAB-MS m/z: 360[M+H]$^+$

EXAMPLE 38 cis-4-[2-(4-chlorostyryl)-6-ethoxyquinazolin-4-yl]
aminocyclohexylamine dihydrochloride Positive ion FAB-MS m/z: 423[M+H]$^+$ Orange yellow powder

EXAMPLE 39 cis-4-aminomethyl-N-[2-(4-chlorostyryl)-6-methoxyquinazolin-4-yl]cyclohexylamine dihydrochloride Positive ion FAB-MS m/z: 423[M+H]$^+$

EXAMPLE 40 cis-4-{6-methyl-2-[2-(2-pyridyl) ethenyl]quinazolin-
4-yl}aminocyclohexylamine Trihydrochloride Positive ion FAB-MS m/z: 360[M+H]$^+$

EXAMPLE 41 cis-4-[2-(4-chlorostyryl)-6-isopropyloxyquinazolin-
4-yl]aminocyclohexylamine dihydrochloride Positive ion FAB-MS m/z: 437[M+H]$^+$ Yellowish white powder

EXAMPLE 42 cis-4-amino-N-[2-(4-chlorostyryl)-6-methoxyquinazolin-4-yl]—N-methylcyclohexylamine dihydrochloride Positive ion FAB-MS m/z: 423[M+H]$^+$

EXAMPLE 43 cis-4-{6-methoxy-2-[2-(3-pyridyl) ethenyl]quinazolin-4-yl}aminocyclohexylamine Trihydrochloride Positive ion FAB-MS m/z: 376[M+H]$^+$

EXAMPLE 44 cis-4-{6-methoxy-2-[2-(2-pyridyl) ethenyl]quinazolin-4-yl}aminocyclohexylamine Trihydrochloride Positive ion FAB-MS m/z: 376[M+H]$^+$

EXAMPLE 45 cis-4-{6-methoxy-2-[2-(4-pyridyl) ethenyl]quinazolin-4-yl}aminocyclohexylamine Trihydrochloride Positive ion FAB-MS m/z: 376[M+H]$^+$

EXAMPLE 46 cis-4-amino-cis-3-methyl-N-[2-(4-chlorostyryl)-6-methoxyquinazolin-4-yl]cyclohexylamine Positive ion FAB-MS m/z: 423[M+H]$^+$ Appearance: White powder

EXAMPLE 47 cis-4-[2-(4-chlorostyryl)-6-hydroxyquinazolin-4-yl]
aminocyclohexylamine dihydrochloride Positive ion FAB-MS m/z: 395[M+H]$^+$ Pale yellow powder

EXAMPLE 48 cis-4-amino-cis-2-methyl-N-[2-(4-chlorostyryl)-6-methoxyquinazolin-4-yl]cyclohexylamine Positive ion FAB-MS m/z: 423[M+H]$^+$ Appearance: White powder

EXAMPLE 49 cis-4-[2-(2-chlorostyryl)-6-methoxyquinazolin-4-yl]
aminocyclohexylamine dihydrochloride Positive ion FAB-MS m/z: 409[M+H]$^+$

EXAMPLE 50 cis-4-amino-cis-2-methyl-N-{6-methoxy-2-[2-(3-pyridyl) ethenyl]quinazolin-4-yl}cyclohexylamine Trihydrochloride Positive ion FAB-MS m/z: 390[M+H]$^+$ Appearance: Pale yellow powder

EXAMPLE 51 cis-4-amino-cis-2-methyl-N-{6-methoxy-2-[2-(2-pyridyl) ethenyl]quinazolin-4-yl}cyclohexylamine Trihydrochloride Positive ion FAB-MS m/z: 390[M+H]$^+$ Appearance: Pale yellow powder

EXAMPLE 52 cis-4-amino-cis-2-methyl-N-{6-methyl-2-[2-(6-methyl-2-pyridyl) ethenyl]quinazolin-4-yl}cyclohexylamine Trihydrochloride Positive ion FAB-MS m/z: 388[M+H]$^+$

EXAMPLE 53 cis-4-{6-chloro-2-[2-(2-pyridyl) ethenyl]quinazolin-4-yl}aminocyclohexylamine Trihydrochloride Positive ion FAB-MS m/z: 380[M+H]$^+$

EXAMPLE 54

4-{6-methyl-2-[2-(2-pyridyl) ethenyl]quinazolin-4-yl}aminomethylbenzylamine Trihydrochloride Positive ion FAB-MS m/z: 382[M+H]$^+$ Appearance: Yellow powder

EXAMPLE 55

2-{6-methyl-2-[2-(2-pyridyl) ethenyl]quinazolin-4-yl}aminoethoxyethylamine trihydrochloride Positive ion FAB-MS m/z: 350[M+H]$^+$ Appearance: Yellow powder

EXAMPLE 56

2-{6-methoxy-2-[2-(2-pyridyl) ethenyl]quinazolin-4-yl}aminoethylphenylethylamine trihydrochloride Positive ion FAB-MS m/z: 426[M+H]$^+$ Appearance: Yellow powder

EXAMPLE 57

(1R, 2S, 4S)-4-amino-2-methyl-N-{6-methyl-2-[2-(2-pyridyl) ethenyl]quinazolin-4-yl}cyclohexylamine Trihydrochloride Similarly to Example 1 and starting from 100 mg of 4-chloro-6-methyl-2-[2-(2-pyridyl) ethenyl]quinazoline and 80 mg of (1R, 2S, 4S)-4-tert-butoxycarbonylamino-2-methylcyclohexylamine, 60 mg of the intended compound was obtained.

Positive ion FAB-MS m/z: 374[M+H]$^+$ Appearance: Pale yellow powder

Specific optical rotation $[\alpha]_D^{20}$-34.78/MeOH, c=1.058

EXAMPLE 58

(1S, 2R, 4R)-4-amino-2-methyl-N-{6-methyl-2-[2-(2-pyridyl) ethenyl]quinazolin-4-yl}cyclohexylamine Trihydrochloride Similarly to Example 1 and starting from 100 mg of 4-chloro-6-methyl-2-[2-(2-pyridyl) ethenyl]quinazoline and 80 mg of (1S, 2R, 4R)-4-tert-butoxycarbonylamino-2-methylcyclohexylamine, 55 mg of the intended compound was obtained.

Positive ion FAB-MS m/z: 374[M+H]$^+$ Appearance: Pale yellow powder

Specific optical rotation $[\alpha]_D^{20}$=+36.82/MeOH, c=0.983

FORMULATION EXAMPLE 1

100 g of the compound of Example 40, 292 g of D-mannitol, 120 g of a corn starch and 28 g of low-substituted hydroxypropyl cellulose are charged into a fluidized bed granulating drier (STREA; POWREX) and granulated with spraying a certain amount of a 5% aqueous solution of hydroxypropyl cellulose. After drying, a pulverizing sizing machine (COMIL; POWREX) is used for sizing the granule, which is subjected to a mixer (Bohle Container Mixer, Model MC; KOTOBUKI ENGINEERING & MANUFACTORING CO., LTD.) to mixing with a certain amount of magnesium stearate, and then subjected to a rotary tabletting machine (CORRECT, 12HUK; KIKUSUI) to shape into a 140 mg-tablet whose diameter is 7 mm, whereby obtaining a tablet containing 25 mg of the present compound.

FORMULATION EXAMPLE 2

75 g of the compound of Example 40, 180 g of lactose, 75 g of corn starch and 18 g of calcium carmellose are charged into a stirring granulator (Vertical Granulator Model VG-01), combined with a certain amount of a 5% aqueous solution of hydroxypropylmethyl cellulose to effect a granulation, and then dried by a fluidized bed granulating drier (STREA; POWREX) and then milled by a pulverizing sizing machine (COMIL; POWREX). 120 mg of the sized material is charged into a No.3 capsule using a capsule filling machine (Capsule Filler; Shionogi Qualicaps Co., Ltd.), whereby obtaining a capsule containing 25 mg of present compound.

FORMULATION EXAMPLE 3

2.5 g of the compound of Example 40 and 4.5 g of sodium chloride are weighed and dissolved in 450 ml of a water for injection with stirring, and adjusted at pH 6.5 with 0.1 mol/L hydrochloric acid or 0.1 mol/L sodium hydroxide. Subsequently, the water for injection is added to make the final volume 500 mL. The solution thus prepared is filtered under pressure through a membrane filter (pore size: 0.22 μm). 5.3 mL of the solution is then filled into a 5 mL brown ampoule aseptically, whereby obtaining an injection formulation containing 25 mg of the present compound. The procedure from the preparation through the filling are conducted in an aseptic manner.

FORMULATION EXAMPLE 4

99.75 g of WITEPSOL H-15 (Huls) is melted at 45° C. and combined with 0.25 g of the compound of Example 40 and dispersed with stirring. The mass is infused into a 1 g suppository mold carefully to prevent any warm sedimentation, and then solidified and released from the mold, whereby obtaining a suppository containing 25 mg of the present compound.

EXPERIMENT EXAMPLE 1

Mouse Formalin Test

A male ddy strain mouse (4 to 5 weeks old) was kept at a temperature of 21 to 25° C. and a humidity of 45 to 65% in a breeding room under the conditions of a constant lighting cycle (light: 12 hours, dark: 12 hours) while allowing the animal to access a feed and water ad libitum, whereby acclimatizing the animal over a period of 1 week or longer. Each 6 to 7 animals were assigned to each group.

After the mouse was acclimatized to an observation cage sufficiently, it was treated with a test compound, and then after 15 minutes 20 μl of 1% formalin solution was given subcutaneously to a hind limb. The test compound was dissolved in a saline, and immediately given to the mouse subcutaneously at the dose of 0.1 ml per 10 g body weight using a 27G needle. A control group received the physiological saline. The animals were returned to their observation cages, and examined for the duration of the aversive responses such as licking or biting the posterior limb using a stopwatch over a period of 30 minutes. The duration of the aversive response observed during the period from 0 to 10 minutes was designated as phase 1, while the duration of the aversive response observed during the period from 10 to 30 minutes was designated as phase 2, and the effect of the compound on the duration in each phase was evaluated.

The results are indicated as mean and standard error. The significance of the difference was analyzed by the one-way layout analysis of variance between the control group and a treatment group followed by Dunnett's multiple comparison. The results are shown in Table 1.

TABLE 1

| Period after formalin treatment (min) | Duration of the abersive response (sec) | | | |
|---|---|---|---|---|
| | Control | Example 1 30 mg/kg n = 6 | Example 40 30 mg/kg n = 6 | Example 52 30 mg/kg n = 7 |
| 0~10 | 142.5 (16.6) | 47.5** (9.3) | 64.5** (7.4) | 79.4** (9.4) |
| 10~30 | 220.7 (38.1) | 74.5* (17.0) | 77.6* (11.5) | 77.0** (17.9) |

( ): Standard error of mean.
*P < 0.05,
**P < 0.01 (vs control by Dunnett's multiple comparison)

As evident from the table shown above, each inventive compound reduced the duration of the aversive response and had an analgesic effect.

EXPERIMENT EXAMPLE 2

Nociceptin Receptor Binding Test

A suspension of cell membrane obtained from a human nociceptin receptor expressing cell was adjusted at a protein concentration of 5 to 10 μg/ml using a Tris-buffer solution [50 mM Tris-HCl (pH 7.8), 5 mM $MgCl_2$, 1 mM EGTA, 0.1% BSA]. The solution was incubated with [$^3$H]-nociceptin (diluted at the final concentration of 0.08 nM using Tris-buffer) and a test compound at 25° C. for 60 minutes. The membrane was recovered using a cell harvester onto a glass fiber (GF) filter GF/B which had previously been treated with 0.3% polyethyleneimine (PEI), and then washed further 4 times with a washing solution[50 mM Tris-HCl (pH 7.8), 4° C.]. The filter was transferred into a counteing vial. Adequate amount of scintillator was added to the vial and the radioactivity was measured using a liquid scintillation counter. A non-specific binding was regarded as a binding of [$^3$H]-nociceptin in the presence of 10 μM nociceptin, and a specific binding was regarded as the difference between the total binding and the non-specific binding. Based on the % binding inhibition in the presence of the test compound, an $IC_{50}$ value was determined, and used together with the Kd value of [$^3$H]-nociceptin for calculating the Ki value of the test compound.

The results are shown in Table 2.

TABLE 2

| Example No. | Nociceptin receptor Ki (μM) | μ preceptor Ki (μM) |
|---|---|---|
| Example 1 | 0.004 | 0.207 |
| Example 22 | 0.029 | 0.313 |
| Example 25 | 0.110 | 0.204 |
| Example 40 | 0.018 | 0.288 |
| Example 44 | 0.023 | 0.492 |
| Example 51 | 0.006 | 0.206 |
| Example 57 | 0.042 | 0.284 |
| Example 58 | 0.002 | 0.234 |

Each inventive compound exhibited a potent binding capacity to the nociceptin receptor.

EXPERIMENT EXAMPLE 3

μ Receptor Binding Test

A nociceptin receptor is a member of an opioid receptor family. An inventive compound was examined for its binding capacity to a μ receptor which is also a member of an opioid receptor family and which is involved in an analgesic effect and a dependency, and compared with the binding capacity to the nociceptin receptor.

A human μ receptor expressing cell membrane preparation (Receptor Biology, Inc) was adjusted at the protein concentration of 8.5 μg/ml using a Tris-buffer solution [50 mM Tris-HCl (pH 7.8), 5 mM $MgCl_2$, 1 mM EGTA, 0.1% BSA]. The solution incubated with [$^3$H]-diprenorphine (diluted at the final concentration of 0.13 nM using Tris-buffer) and a test compound at 25° C. for 90 minutes. The membrane was recovered using a cell harvester onto a GF/B filter which had previously been treated with 0.3% PEI, and then washed further 4 times with a washing solution [50 mM Tris-HCl (pH 7.8), 4° C.]. The filter was transferred into a counting vial. Adequate amount of scintillator was added and the radioactivity was measured using a liquid scintillation counter. A non-specific binding was regarded as a binding of [$^3$H]-diprenorphine in the presence of 100 μM naloxone, and a specific binding was regarded as the difference between the total binding and the non-specific binding. Based on the % binding inhibition in the presence of the test compound, an $IC_{50}$ value was determined, and used together with the Kd value of [$^3$H]-diprenorphine for calculating the Ki value of the test compound.

The results are shown in Table 2.

Each inventive compound exhibited a μ receptor binding ability which was lower than the binding capacity to the nociceptin receptor.

Based on the results of Experiment Examples 2 and 3, each inventive compound was proven to have a high selectivity to the nociceptin receptor.

INDUSTRIAL APPLICABILITY

A Compound (I) according to the invention having an excellent analgesic effect can be used safely for a prolonged period as a therapeutic agent against a disease accompanied with a pain, such as, migraine, rheumatoid arthritis, neualgia and the like as well as an overcoming agent for tolerance by morphine or other substances. As the compound shows a nociceptin binding ability, it is useful also against a chronic pain or an allodynia associated with a herpes zoster.

The invention claimed is:

1. A pharmaceutical composition for use as an analgesic, diuretic, anesthetic, antihypertensive, arixiolytic, antiobese agent, auditory controlling agent anti-depressive, anti-dementia agent or opicid analgesic tolerance-overcoming agent containing as an active ingredient a compound represented by Formula (I) or a salt thereof:

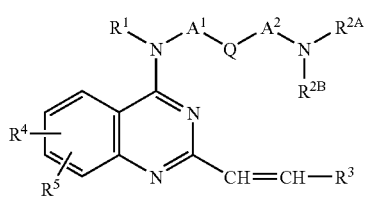

(I)

wherein $R^1$ represents a hydrogen atom or alkyl;

$A^1$ and $A^2$ represent a single bond;

Q represents an optionally substituted 3- to 8-membered cycloatkylene group;

$R^{2A}$ and $R^{2B}$ are the same or different and each represents a hydrogen atom or alkyl;

$R^3$ represents an optionally substituted phenyl group or heterocydic group;

$R^4$ and $R^5$ are the same or different and (1) each represents a hydrogen atom, alkyl, altoxy, aralkyloxy, halogen, nitro, hydroxy, alkoxycarbonyl, —$NR^6R^7$, —$NR^6COR^7$, —$NR^6SO_2R^7$, —$CONR^6R^7$, wherein $R^6$ and $R^7$ are the same or different and each represents a hydrogen atom or alkyl) or (2) adjacent $R^4$ and $R^5$ are taken together to form —$O(CH_2)_nO$, wherein n is an integer of 1 or 2, or —C=CH—CH.

2. The pharmaceutical composition according to claim 1, wherein $R^1$ represents a hydrogen atom or an alkyl of 1 to 4 carbon atoms, $R^{2A}$ and $R^{2B}$ represent hydrogen atoms, $R^3$ represents a phenyl group or heterocyclic group optionally substituted by alkyl, alkoxy, alkoxycarbonyl, amino, monoalkylamino, dialkylamino, nitro, halogen, cyano or hydroxy, $R^4$ and $R^5$ are the same or different and each represents a hydrogen atom, alkyl, alkoxy, aralkyloxy, halogen, nitro, hydroxy, alkoxycarbonyl, —$NR^6R^7$, $NHCOR^6$, —$NHSO_2R^6$, or —$CONR^6R^7$, wherein $R^6$ and $R^7$ are the same or different and each represents a hydrogen atom or alkyl, $A^1$ and $A^2$ represents a single bond, Q represents a 4- to 8-membered cycloalkylene group optionally substituted by alkyl, alkoxycarbonyl, carbamoyl, monoalkylcarbamoyl, dialkylcarbamoyl or alkoxy.

3. The pharmaceutical composition according to claim 1, wherein $R^1$ represents a hydrogen atom or an alkyl of 1 to 3 carbon atoms, $R^{2A}$ and $R^{2B}$ represent hydrogen atoms, $R^3$ represents a phenyl group or heterocyclic group optionally substituted by alkyl, alkoxy, amino, monoalkylamino, dialkylainino, halogen, cyano or hydroxy, $R^4$ and $R^5$ are the same or different and each represents a hydrogen atom, alkyl, alkoxy, aralkyloxy, halogen, hydroxy, alkoxycarbonyl, —$NR^6R^7$, —$NHCOR^6$, wherein $R^6$ and $R^7$ are the same or different and each represents a hydrogen atom or alkyl, each of $A^1$ and $A^2$ represent a single bond, Q represents a 4- to 8-membered cycloalkylene group optionally substituted by alkyl, alkoxycatbonyl, carbainoyl, monoalikylcarbamoyl, dialkylcarbamoyl or alkoxy.

4. The pharmaceutical composition according to claim 1, wherein the active ingredient is selected from the group consisting of cis-4-amino-cis-2-methyl-N-{6-methyl-2-[2-(2-pyridyl) ethenyl]quinazolin-4-yl}cyclohexylainine trihydrochioride, cis-4[-2-(4chlorostyryl)-6-methylquinazolin-4-yl]aminocyclohexylamine dihydrochioride, cis-2-[2-(4-chlorostyryl)-6-methoxyquinazolin-4-yl] aminocyclohexylamine dihydrochioride, cis-4-{6-methyl-2-[2-(2-pyridyl) ethenyl]quinazolin-4-yl}aminocyclohexylamine trihydrochioride, cis-4-{6-methoxy-2-[2-(2-pyridyl) ethenyl]quinazolin-4-yl }aminocyclohexylainine trihydrochioride, cis-4-amino-cis-2-methyl-N-[2-(4-chlorostyryl)-6-methoxyquinazolin-4-yl]cyclohexylamine, cis-4-amino-cis-2-methyl-N-{6-methoxy-2-[2-(3-pyridyl) ethenyl]quinazolin -4-yl}cyclohexylamine trihydrochioride, cis-4-amino-ois-2-methyl-N-{6-methoxy-2-[2-(2-pyridyl) ethenyl]quinazolin-4-yl}cyclohexylamine trihydrochlofide, cis-4-amino-cis-2-methyl -N-{6-methyl-2-[2-(6-methyl-2-pyridyl) ethenyl]quinazolin-4-yl}cyclohexylamine trihydrochloride, (1R, 2S, 4S)-4-amino-2-methyl-N-{6-methyl-2-[2-(2-pyridyl) ethenyl] quinazolin-4-yl}cyclohexylaxnine trihydrochloride and (1S, 2R, 4R)-4-amino-2-methyl-N-{6-methyl-2-[2-(2-pyridyl) ethenyl]quinazolin-4-yl}cyclohexylamine trilxydrochloride.

5. A compound represented by Formula (Ia) or a salt thereof:

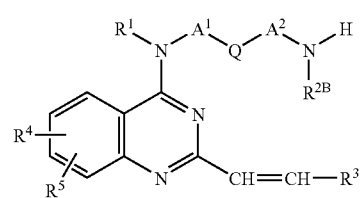

(Ia)

wherein:

$R^1$ represents a hydrogen atom or alkyl;

$A^1$ and $A^2$ represent a single bond;

Q represents an optionally substituted 3- to 8-membered eycloalkylene group;

$R^{2B}$ represents a hydrogen atom or alkyl;

$R^3$ represents an optionally substituted phenyl group or heterocyclic group;

$R^4$ and $R^5$ are the same or different and (1) each represents a hydrogen atom, alkyl, alkoxy, aralkyloxy, halogen, nitro, hydroxy, alkoxycarbonyl, —$NR^6R^7$, —$NR^6COR^7$, —$NR^6SO_2R^7$, —$CONR^6R^7$, wherein $R^6$ and $R^7$ are the same or different and each represents a hydrogen atom or alkyl or (2) adjacent $R^4$ and $R^5$ are taken together to form —$O(CH_2)_nO$—, wherein n is an integer of 1 or 2, or —CH=CH—CH=CH—.

6. The compound according to claim 5 or a salt thereof, wherein $R^1$ represents a hydrogen atom or an alkyl of 1 to 4 carbon atoms, $R^{2B}$ represents a hydrogen atom, $R^3$ represents a phenyi group or heterocyclic group optionally substituted by alkyl, alkoxy, alkoxycarbonyl, amino, monoalkylanilno, dialkylamino, nitro, halogen, cyano or hydroxy, $R^4$ and $R^5$ are the same or different and each represents a hydrogen atom, alkyl, alkoxy, aralkyloxy, halogen, nitro, hydroxy, aikoxycarbonyl, —$NR^6R^7$, $NHCOR^6$, -$NHSO2R^6$, $NHSO_2R^6$ or —$CONR^6R^7$, wherein $R^6$ and $R^7$ are the same or different and each represents a hydrogen atom or alkyl, $A^1$ and $A^2$ represent a single bond, Q represents a 4- to 8-membered cycloalkylene group optionally substituted by alkyl, alkoxycarbonyl, carbamoyl, monoalkylcarbamoyl, dialkylcarbamoyl or alkoxy.

7. The compound according to claim 5 or a salt thereof wherein $R^1$ represents a hydrogen atom or an alkyl of 1 to 3 carbon atoms, $R^{2B}$ represents a hydrogen atom, $R^3$ represents a phenyl group or heterocyclic group optionally substituted by alkyl, alkoxy, amino, monoalkylamino, dialkylamino, halogen, cyano or hydroxy, $R^4$ and $R^5$ are the same or different and each represents a hydrogen atom, alkyl, alkoxy, aralkyloxy, halogen, hydroxy, alkoxycarbonyl, —$NR^1R^7$, $NHCOR^6$, wherein $R^6$ and $R^7$ are the same or different and each represents a hydrogen atom or alkyl, each of $A^1$ and $A^2$ represents (1) a single bond, Q represents a 4- to 8-membered cycloalkylene group optionally substituted by alkyl, alkoxycarbonyl, carbamnoyl, monoalkylcarbamoyl, dialkylcarbamoyl or alkoxy.

8. The compound according to claim 1 or a salt thereof, which is selected from the group consisting of cis-4-amino-cis-2-methyl-N-{6-methyl-2-[2-(2-pyridyl) ethenyl] quinazolin-4-yl}cyclohexylamine trihydrochloride, cis-4-[2-(4-chlorostyryl)-6-methylquinazolin-4-yl] aminocyclohexylamine dihydroehioride, cis-2-[2-(4-chlorostyryl)-6-methoxyquinazolin-4-yl] aminocyclohexylarnine dihydrochioride, cis-4-{6-methyl-2-[2-(2-pyridyl) ethenyl]quinazolin-4-yl}aminocyclohexylamine trihydrochioride, cis-4-{6-methoxy-2-[2-(2-pyridyl) ethenyl]quinazolin-4-yl}aminocyclohexytamine trihydrochloride, cis-4-amino-cis-2-methyl-N- [2-(4-chlorostyryl)-6-methoxyquinazolin-4-yl]cyclohexylainine, cis-4-amino-cis-2-methyl-N-{6-methoxy-2-[2-(3-pyridyl) etheny]quinazolin-4-yl}cyclohexylamine trihydrochloride, cis-4-amino-cis-2-methyl-N-{6-methoxy-2-[2-(2-pyridyl) ethenyl]quinazolin-4-yl}cyclohexylamine trihydrochloride, cis-4-amino-cis-2-methyl-N-{6-methyl-2-[2-(6-methyl-2-pyridyl) ethetiyl] quinazolin-4-yl}cyclohexylamine trihydrochioride, (1R, 2S, 4S)-4-amino-2-methyl-N-{6-methly-2-[2-(2-pyridyl) ethenyl]quinazolin-4-yl}cyclohexylamine trihydrochioride and (1S, 2R, 4R)-4-amino-2-methyl-N-{6-methyl-2-[2-(2-pyridyl) ethenyl]quinazolin-4-yl}cyclohexylanine trihydrochioride.

9. A pharmaceutical composition comprising as an active ingredient the compound according to claim 5 or a salt thereof.

\* \* \* \* \*